US008922646B2

(12) United States Patent
Neckels et al.

(10) Patent No.: US 8,922,646 B2
(45) Date of Patent: Dec. 30, 2014

(54) CALCULATE DROP DELAY FOR FLOW CYTOMETRY SYSTEMS AND METHODS

(75) Inventors: David Neckels, Berthoud, CO (US); Kevin Courter, Fort Collins, CO (US)

(73) Assignee: Beckman Coulter, Inc., Brea, CA (US)

(*) Notice: Subject to any disclaimer, the term of this patent is extended or adjusted under 35 U.S.C. 154(b) by 966 days.

(21) Appl. No.: 13/043,781

(22) Filed: Mar. 9, 2011

(65) Prior Publication Data

US 2011/0221892 A1      Sep. 15, 2011

Related U.S. Application Data

(60) Provisional application No. 61/311,956, filed on Mar. 9, 2010.

(51) Int. Cl.
*H04N 7/18*       (2006.01)
*G01N 15/14*      (2006.01)

(52) U.S. Cl.
CPC ...... *G01N 15/1427* (2013.01); *G01N 2015/149* (2013.01); *G01N 2015/1406* (2013.01)
USPC ........... 348/135; 382/128; 382/133; 382/170; 382/183; 436/50; 436/63; 436/164

(58) Field of Classification Search
CPC .................. G01N 2015/14; G01N 2015/1406; G01N 2015/149; G01N 15/1427; G01N 15/1404; G01N 15/1425; G01N 15/1459; G01N 15/1463; G01N 15/1475; G01N 15/0065; G01N 2015/1443; G01N 21/6458; G01N 2021/6441; G01N 21/6428; G01N 33/533; G01N 33/569; G01N 33/582; G01N 15/14
USPC .............. 382/128, 133, 170, 183; 436/50, 63, 436/164

See application file for complete search history.

(56) References Cited

U.S. PATENT DOCUMENTS

| 4,361,400 | A | 11/1982 | Gray et al. |
|---|---|---|---|
| 5,643,796 | A | 7/1997 | Van den Engh et al. |
| 6,248,590 | B1 | 6/2001 | Malachowski |
| 6,372,506 | B1 | 4/2002 | Norton |
| 6,589,792 | B1 | 7/2003 | Malachowski |
| 6,809,804 | B1 | 10/2004 | Yount et al. |
| 6,941,005 | B2 * | 9/2005 | Lary et al. ..................... 382/133 |

(Continued)

FOREIGN PATENT DOCUMENTS

WO      WO2009078307      6/2009

OTHER PUBLICATIONS

Mathcentre, 2009.*

*Primary Examiner* — Sath V Perungavoor
*Assistant Examiner* — Nathnael Aynalem
(74) *Attorney, Agent, or Firm* — K&L Gates LLP; Louis C. Cullman; Georgia Kefallinos

(57) ABSTRACT

A method of calculating a drop delay in a stream of a flow cytometer. In one embodiment the method includes the steps of determining a widths plot by measuring the width of a stream based on an image of the stream and setting drop delay based on the widths plot. In another aspect the invention relates to a flow cytometer system for automatically calculating drop delay. In one embodiment the flow cytometer system includes means for determining a widths plot based on an image of the stream; and means for calculating drop delay based on the widths plot.

19 Claims, 17 Drawing Sheets

(56) References Cited

U.S. PATENT DOCUMENTS

| | | |
|---|---|---|
| 7,417,734 B2 | 8/2008 | Kanda |
| 2002/0015088 A1* | 2/2002 | Inoue et al. ......... 347/238 |
| 2002/0093641 A1* | 7/2002 | Ortyn et al. ......... 356/28 |
| 2005/0042760 A1 | 2/2005 | Yount et al. |
| 2005/0110996 A1 | 5/2005 | Sharpe |
| 2010/0284016 A1* | 11/2010 | Teitell et al. ......... 356/451 |

* cited by examiner

CALCULATE DROP DELAY FOR FLOW CYTOMETRY SYSTEMS AND METHODS

PRIORITY CLAIM

This patent application claims priority pursuant to 35 U.S.C. §119(e) to U.S. Provisional Patent Application 61/311,956, filed on Mar. 9, 2010, which is hereby incorporated by reference in its entirety.

BACKGROUND

1. Field of the Invention

The present invention relates to systems and methods for flow cytometry. More specifically, the present invention relates to systems and methods for calculating drop delay in a flow cytometer.

2. Background Art

In the field of flow cytometry, a hydrodynamic focusing technique is used to separate and align analyte particles within a stream. An oscillator perturbs the stream as it is released from a nozzle of the flow cytometer. The perturbation results in droplets containing individual analyte particles. Just prior to breaking off from the stream, the droplets can be electrically charged and an electrical field downstream from the break-off point can be used to deflect and sort the charged particle. As part of this process, it is necessary to determine the system's "drop delay" (i.e., the time between when a particle of interest is identified, to when a droplet containing the particle of interest reaches the charging location (or "break-off point")). As such, the droplet of interest can be charged without affecting neighboring droplets.

Commercial flow cytometers typically use empirical, iterative, trial-and-error protocols to determine drop delay. For example, fluorescent beads can be run through the flow cytometer while a user (or automated program) cycles through a range of drop delay settings. When the user (or automated program) finds the drop delay setting resulting in the optimal sorting of the fluorescent beads, such drop delay is set as the operational drop delay, and is used for the sample runs. Use of fluorescent beads to determine drop delay, however, is undesirable because fluorescent beads can contaminate the flow cytometer. Further, what are needed are systems and methods to avoid the use of iterative, trial-and-error operations, which are time-consuming and can lack the necessary precision of drop delay calculation.

The systems and methods presented herein act to solve some of the problems seen in the prior art. It is noted that the systems and methods presented herein do not merely automate a previously manual process. The systems and methods presented herein have been developed through painstaking design, testing, and optimization. Challenges in achieving the necessary precision were identified and addressed in the development of these systems and methods. As such, the systems and methods presented herein provide significantly higher accuracy than prior art systems.

BRIEF SUMMARY

The invention relates to a method of calculating a drop delay in a stream of a flow cytometer. In one embodiment the method includes the steps of determining a widths plot by measuring the width of a stream based on an image of the stream and setting drop delay based on the widths plot.

In another, embodiment the method of calculating a drop delay in a stream of a flow cytometer includes identifying a laser position relative to a frame of reference; determining break-off point; and calculating drop delay by setting a strobe phase, imaging the stream, determining a widths plot by measuring the widths of the stream based on the image of the stream, determining the peaks in the widths plot, calculating phase of laser intercept, and setting drop delay in response to the peaks in the widths plot, a phase of the laser intercept relative to a droplet generation wave and a charge phase. In one embodiment the method includes smoothing the widths plot. In another embodiment the method includes calculating a derivative of the widths plot, and recording a plurality of zero-crossings of the derivative, wherein each zero-crossing is indicative of a peak in the widths plot, In yet another embodiment the break-off point is the shortest break-off point. In still yet another embodiment the step of imaging the stream includes the steps of running a camera along a length of the stream, while taking a plurality of images of the stream; and stitching the plurality of images together to form a single image. In another embodiment the strobe phase is set to the charge phase plus 180°. In still another embodiment the drop delay is also set in response to a bias correction factor. In yet another embodiment the bias correction factor is equal to a linear function aX+b, where X is the time from nozzle to break-off and parameters "a" and "b" are determined from experimental measurement of system response. In another embodiment the smoothing of the widths plot is conducted using a discrete Fourier analysis. In one embodiment a drive voltage is increased from an operational value when the camera is at about the top of the stream, and the drive voltage is decreased to an operational value as the camera is driven down towards the break-off point. In another embodiment the calculation of drop delay is used to determine when an analyte of interest has reached the break-off point of the stream.

In another aspect the invention relates to a flow cytometer system for automatically calculating drop delay. In one embodiment the flow cytometer system includes means for determining a widths plot based on an image of the stream and means for calculating drop delay based on the widths plot. In another embodiment the flow cytometer system includes means for taking an image of a stream; means for determining a widths plot based on an image of the stream; means for determining peaks in the widths plot and means for calculating drop delay based on the determined peaks. In one embodiment the system includes means for smoothing the widths plot. In another embodiment the system includes means for calculating a derivative on the widths plot; and means for determining zero-crossing on the widths plot. In yet another embodiment the means for taking an image of the stream comprises taking a plurality of images of the stream and the cytometer system further comprises means for stitching the plurality of images of the stream to form one entire image of the stream.

In another embodiment the system includes a camera adapted to take an image of a stream; and a processor adapted to determine a widths plot based on the image of the stream, and adapted to calculate drop delay based on the widths plot. In still yet another embodiment the system includes a camera mounted on a precision-calibrated, movable camera stage, which is adapted to take a plurality of images of a stream; and a processor adapted to stitch the plurality of images of the stream to form one entire image of the stream, determine a widths plot based of the one entire image of the stream, smooth the widths plot, calculate a derivative on the smoothed widths plot, determine zero-crossing on the smoothed widths plot, and calculate drop delay based on the determined zero-crossings.

BRIEF DESCRIPTION OF THE DRAWINGS

The accompanying drawings, which are incorporated herein, form part of the specification and illustrate embodiments of flow cytometer systems and methods for calculating drop delay. Together with the description, the drawings further serve to explain the principles of, and to enable a person skilled in the relevant art(s) to make and use the systems and methods described herein. In the drawings, like reference numbers indicate identical or functionally similar elements.

DETAILED DESCRIPTION

The following detailed description of systems and methods for calculating drop delay refers to the accompanying drawings that illustrate exemplary embodiments. Unless otherwise noted, all embodiments and examples should be considered prophetic examples. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware, software, and/or firmware. Any actual hardware, software, and/or firmware described are not meant to be limiting.

Figure 1:
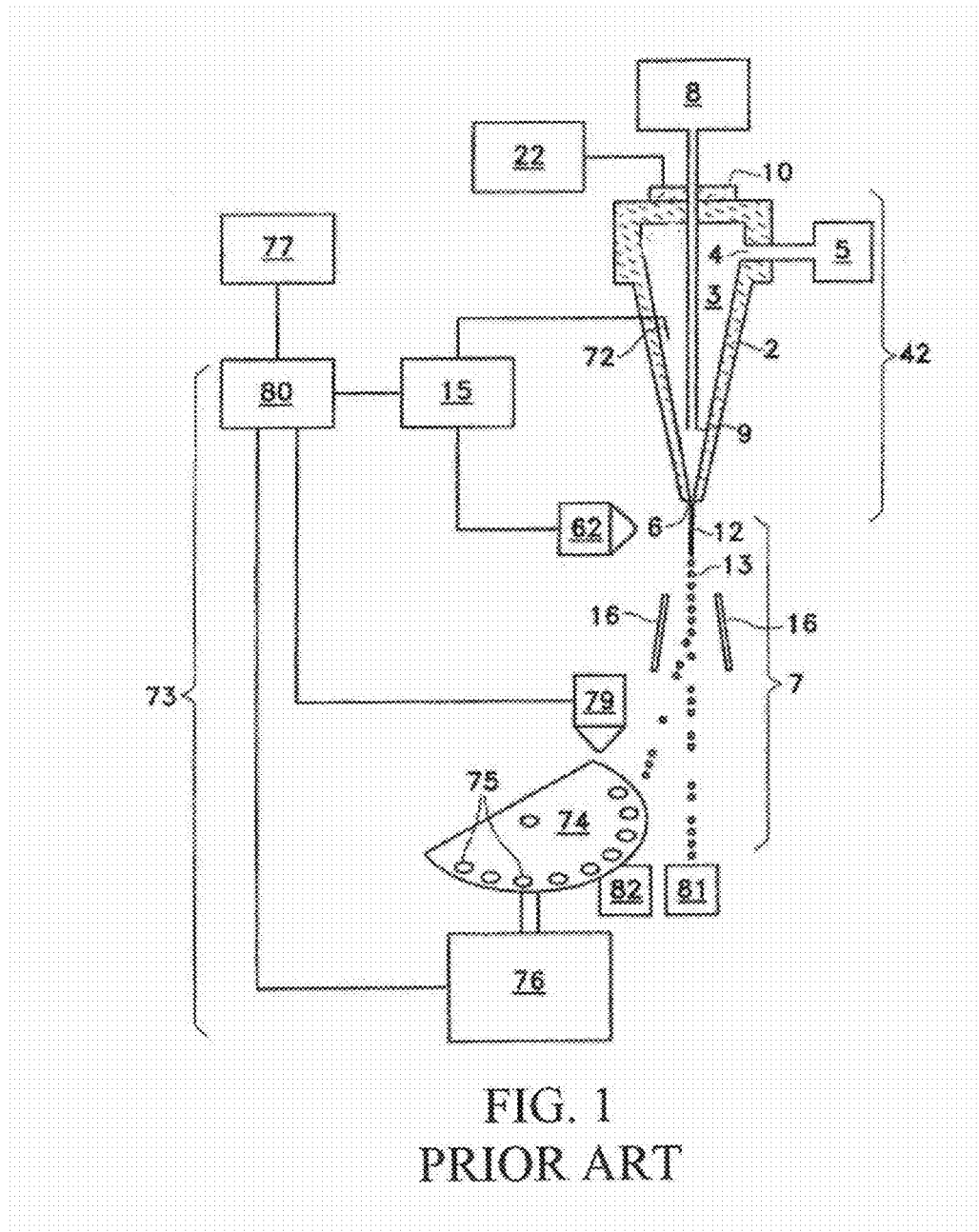
FIG. 1 is a schematic of a prior art flow cytometer system.

FIG. 1 is a schematic of a prior art flow cytometer system, as taught in U.S. Pat. No. 5,643,796, which was incorporated by reference above. FIG. 1 is presented to show the basic parts of a flow cytometer system, which can be employed in the systems and methods of the present invention. FIG. 1, however, is also presented to show a system that employs an iterative, trial-and-error process to calculate drop delay, which is different from the systems and methods of the present invention.

Specifically, FIG. 1 shows a droplet flow cytometer having a nozzle system 42, which in turn includes a nozzle container 2. Introduced within a nozzle volume 3 is sheath fluid from sheath reservoir 5 through sheath fluid port 4. Analyte particles are introduced within the sheath fluid from substance reservoir 8 through substance introduction port 9. The sheath fluid, together with its entrained analyte particles, are hydrodynamically focused so that the individual analyte particles line up in a single-file orientation and are emitted from nozzle exit 6 into free fall area 7.

In order to form regular droplets, an oscillator 10 is adapted to cause pressure waves within, or actual movement of, the sheath fluid. Oscillator 10 is controlled by an alternating voltage source 22. As a result of oscillations within the sheath fluid, stream 12 is periodically perturbed to form droplets 13. Each droplet 13 is analyzed while in stream 12 to assess whether the droplet 13 contains an analyte of interest.

As shown in FIG. 1, substance property sensor 62 is positioned to sense emissions occurring from the analyte within stream 12 just prior to free droplet formation (i.e. at the point where the droplet breaks free from the stream). The signals sensed by substance property sensor 62 are processed by a processor, such as analysis equipment 15. Droplets 13 can then be characterized by components including sorting equipment 16. As shown, sorting equipment 16 creates an electrostatic field so that charged droplets are deflected, whereas uncharged droplets are not. The differential charging of one droplet as opposed to another can be achieved through the interconnection of analysis equipment 15 with electrode 72. Since analysis equipment 15 can obtain its information from substance property sensor 62, electrode 72 can be responsive to substance property sensor 62. Electrode 72 can be positioned within nozzle volume 3 so as to cause a charge on the sheath fluid. Thus, the sheath fluid can be responsive to electrode 72. The charge can be transmitted to the end of stream 12 so that at the instant when a droplet is formed, that droplet can be charged. Electrode 72 can then be quickly neutralized so that the next droplet formed does not get inadvertently charged. In this fashion, when droplets 13 pass through sorting equipment 16, some individual droplets—namely those which do or do not contain the desired substance as determined by analysis equipment 15—will be deflected. The deflected droplet can thus be collected in sample collection container 82, whereas the undeflected droplets can pass to drain receptacle 81. The appropriate timing of the charging of stream 12 through action of electrode 72 requires the accurate utilization of a droplet formation time delay (or "drop delay") estimate; specifically, the amount of time it takes for the droplet to form after substance property sensor 62 and analysis equipment 15 have actually determined whether a droplet 13 in stream 12 contains a desired analyte.

To determine optimal drop delay, the system of FIG. 1 employs an automatic droplet sampler 73 that samples the droplets sorted by sorting equipment 16. Automatic droplet sampler 73 has a plurality of collection areas 75 situated on or supported by movable platter 74. Through moving movable platter 74, different containers 75 can be sequentially positioned in free fall area 7 and thus can gather droplets. Importantly, movable platter 74 can be responsive to stepper 76 so that the various containers 75 can be separately and incrementally positioned in free fall area 7. Thus, throughout one single sampling event, a number of different samples can be taken.

In the system of FIG. 1, a droplet formation time delay adjustment 80 coordinates with automatic droplet sampler 73 to optimize the time delay. Optimization is achieved by creating an automatic substance maximization means—essentially, any component, software, or circuitry which automatically provides information to allow maximization of the substance sorted. The substance maximization means can include increment control 77, a device which acts to automatically adjust the various time delays actually applied by analysis equipment 15 in controlling electrode 72. Through increment control 77, the time delay applied by analysis equipment 15 to electrode 72 can be varied in incremental amount as each different container 75 is positioned within free fall area 7. Thus, each container 75 can represent a different time delay amount. These results can then be used to achieve an optimum (or more optimum) drop formation time delay estimate.

In such an automated configuration, a cell counter 79 yields information that allows time delay adjustment 80 to alter the actual time delay used during processing. In this fashion, different time delay amounts can be applied and tested automatically to see which yields the maximum count.

As would be appreciated by one of skill in the art, despite the fact that the system of FIG. 1 is an automated system, such system proceeds through an iterative, trial-and-error protocol to determine optimal time delay.

Figure 2:
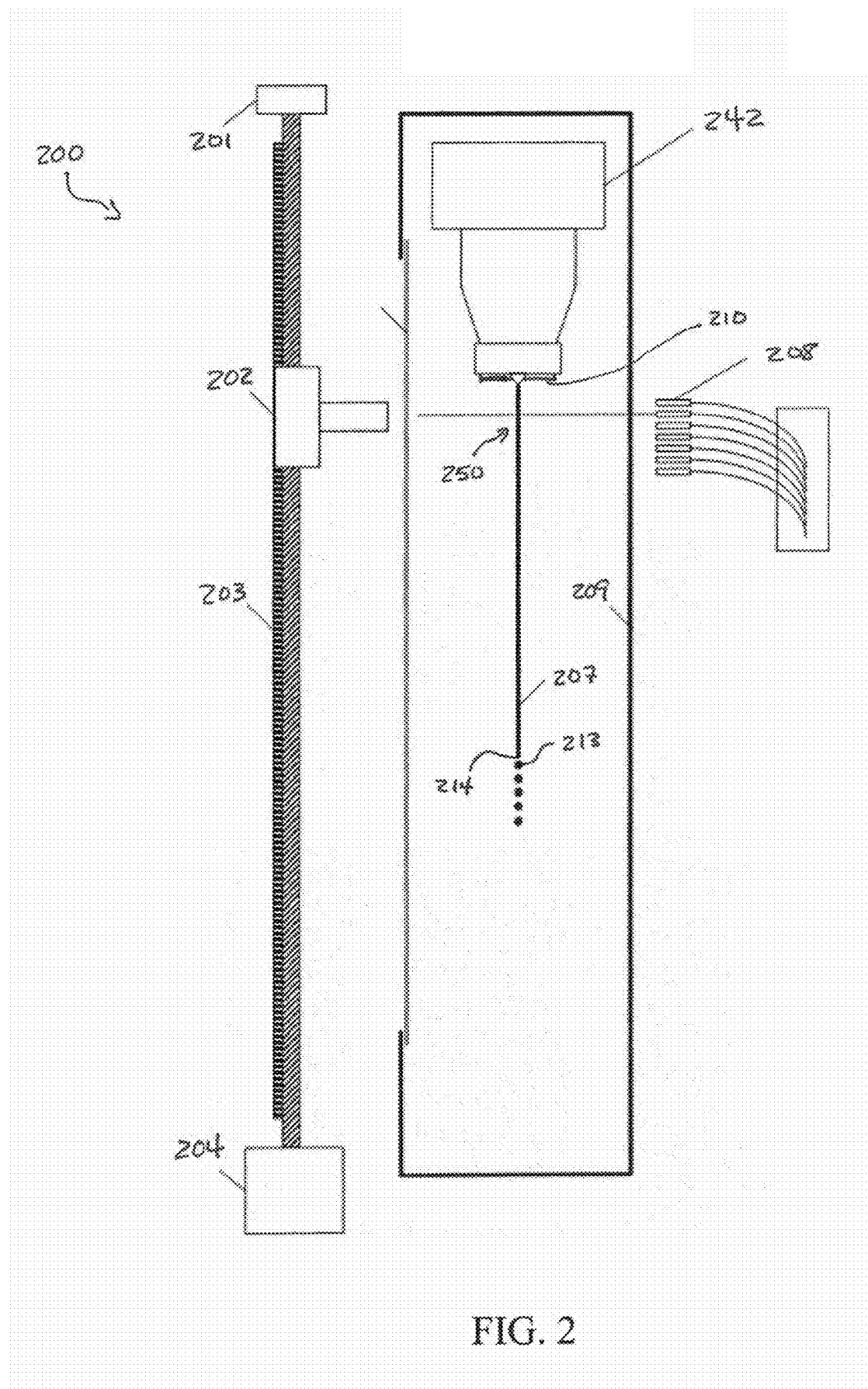
FIG. 2 is a schematic view of a flow cytometer system in accordance with an embodiment of the present invention.

FIG. 2 is a schematic view of a flow cytometer system 200 in accordance with an embodiment of the present invention. As with other flow cytometer systems, flow cytometer 200 includes a nozzle system 242, an oscillator 210, and an interrogation chamber enclosure 209.

Within interrogation chamber enclosure 209, one or more laser sources 208 emit one or more laser beams that cross a stream 207 at laser intercept 250. Detectors (not shown) are used to detect emissions from analyte particles in stream 207. An analysis system (not shown) then determines whether the analyte particle crossing laser intercept 250 is an analyte of interest. Such analysis is typically based on the fluorescence, side scatter, or forward scatter of the analyte particle.

As in typical flow cytometers, oscillator 210 perturbs stream 207 to form droplets 213. In the methods of the present invention, oscillator 210 serves as the reference frequency and reference phase for the calculations of the drop delay. Although illustrated as being connected to the bottom of nozzle system 242, it is understood that the oscillator can be attached to other locations on the nozzle system 242. The time between when an analyte of interest crosses laser intercept 250 and the time the analyte of interest reaches break-off point 214 is the "drop delay," which is typically referenced in periods relative to the frequency of the oscillator 210. Typically, the system has about 400 microseconds to determine whether the analyte particle crossing laser intercept 250 is an analyte of interest.

Unique to the systems of the present invention, flow cytometer 200 includes a precision-calibrated, movable camera stage. In one embodiment, the movable camera stage is a ball screw linear motion stage 201. Mounted on stage 201 is a camera 202. Typically, camera 202 is a high magnification objective camera. In operation, camera 202 is moved along the track of stage 201, and the camera position is measured with stage position measurement capabilities, such as optical encoder 203. Movement of camera 202 is actuated by a precision motor or drive mechanism, such as a servo motor 204.

As further explained below, camera 202 is precisely driven down track 203 in order to obtain a plurality of high-resolution images of stream 207. Specifically, camera 202 is incrementally driven down track 203, taking an image at each increment. The images are then stitched together using digital image processing algorithms. In an alternative embodiment, a wide-angle lens camera can be employed to take an image (or multiple images) of the entire stream 207. As will be fully understood below, while prior art systems use iterative, trial-and-error protocols to determine drop delay, the systems and methods of the present invention calculate drop delay based on the stitched image of stream 207. In essence, the methods presented herein process the stitched image to identify the number of droplets, peaks, and/or periods between laser intercept 250 and break-off point 214. After identifying the number of droplets, peaks, and/or periods between these two points, the system can accurately predict the drop delay by compensating for variables that affect drop delay. As such, the systems and methods of the present invention do not require fluorescent beads, or empirical, iterative protocols.

Figure 7:
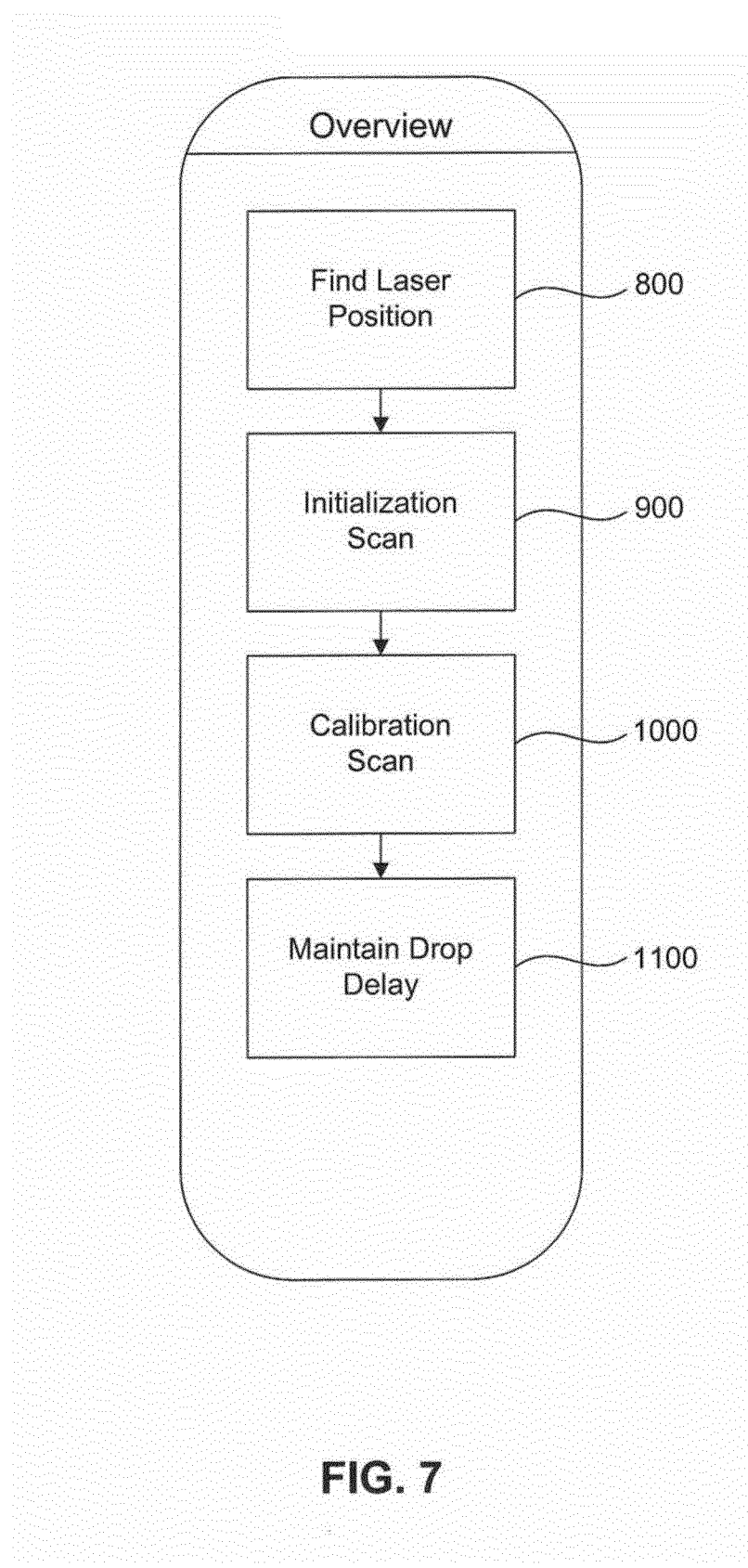
FIG. 7 is a high-level flowchart showing a method presented herein.

FIG. 7 is a high-level flowchart showing a method presented herein. The method of FIG. 7 includes four main sub-methods, namely: a method 800 for precisely finding the laser position of the flow cytometer; a method 900 of conducting an initialization scan; a method 1000 of conducting a calibration scan, in which the drop delay is calculated; and a method 1100 for maintaining the drop delay. Method 1100 for maintaining drop delay is known to those skilled in the art, is not pertinent to the present invention, and is therefore not discussed in any detail in this specification.

Figure 8:
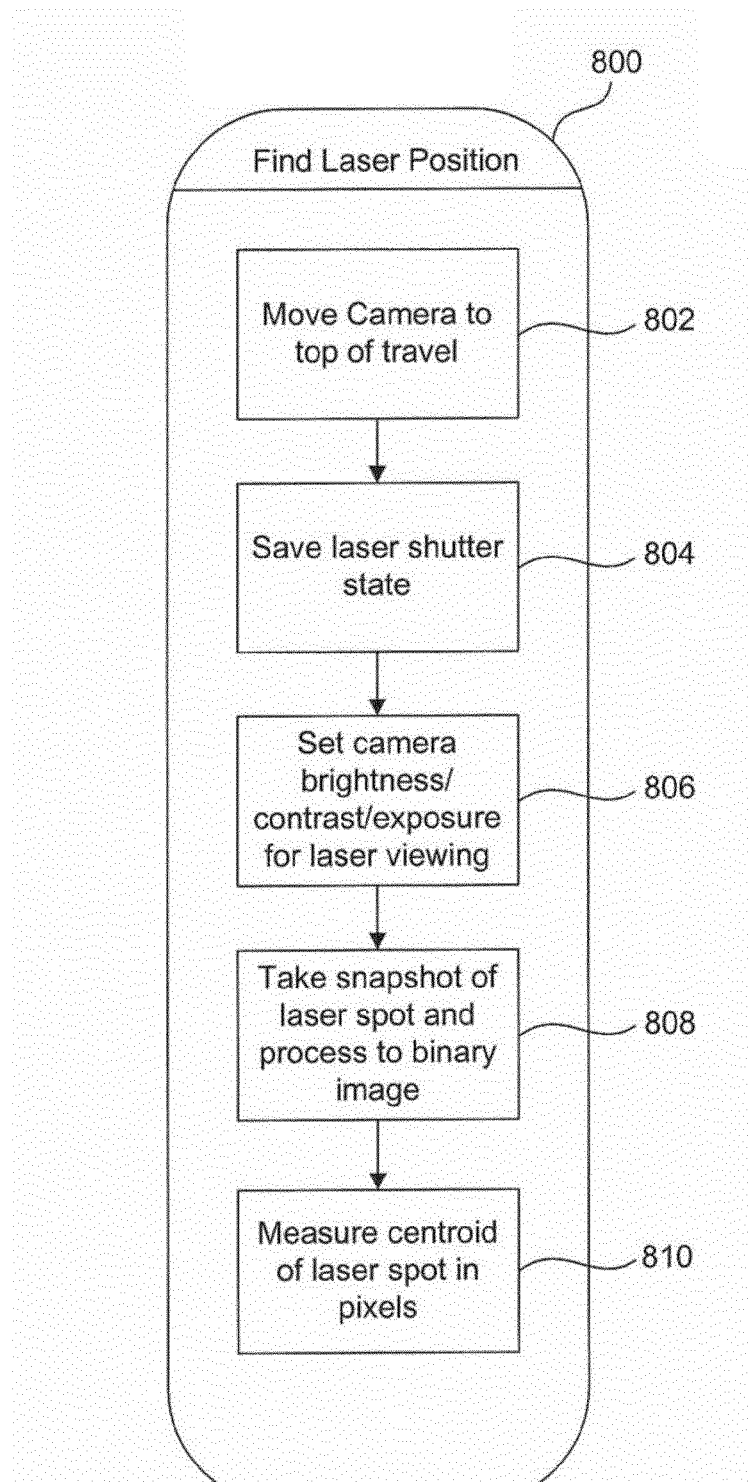
FIG. 8 is a flowchart showing a method of finding a laser position.

FIG. 8 is a flowchart showing method 800 for precisely finding the laser position of the flow cytometer. Typically, upon putting together a flow cytometer, a user does not care where in physical space the laser is located. The user typically only cares that the laser is properly aligned with the stream. For the methods of calculating drop delay in accordance with this invention, however, the exact location of the laser's intercept with the stream is important because the location is a variable in calculating drop delay. With reference to flow cytometer 200 of FIG. 2, method 800 begins at step 802 by first moving camera 202 to the top of travel (i.e., where stream 207 exits nozzle 242). At the top of travel, the precise location of camera 202 is known. The location of camera 202 at the top of travel serves as the reference point for all ensuing calculations. In step 804, the state of the laser shutters is saved such that only the laser of interest in turned on. In step 806, the camera's 202 brightness, contrast, and/or exposure are set for laser viewing. In step 808, a snapshot of the laser is taken, and the image is processed into a binary image. In step 810, the centroid of the laser is measured as a function of image pixels. With the measurement of the laser centroid taken, the exact position of the intercept of the laser with the stream, relative to the camera stage, is known.

Figure 9A:
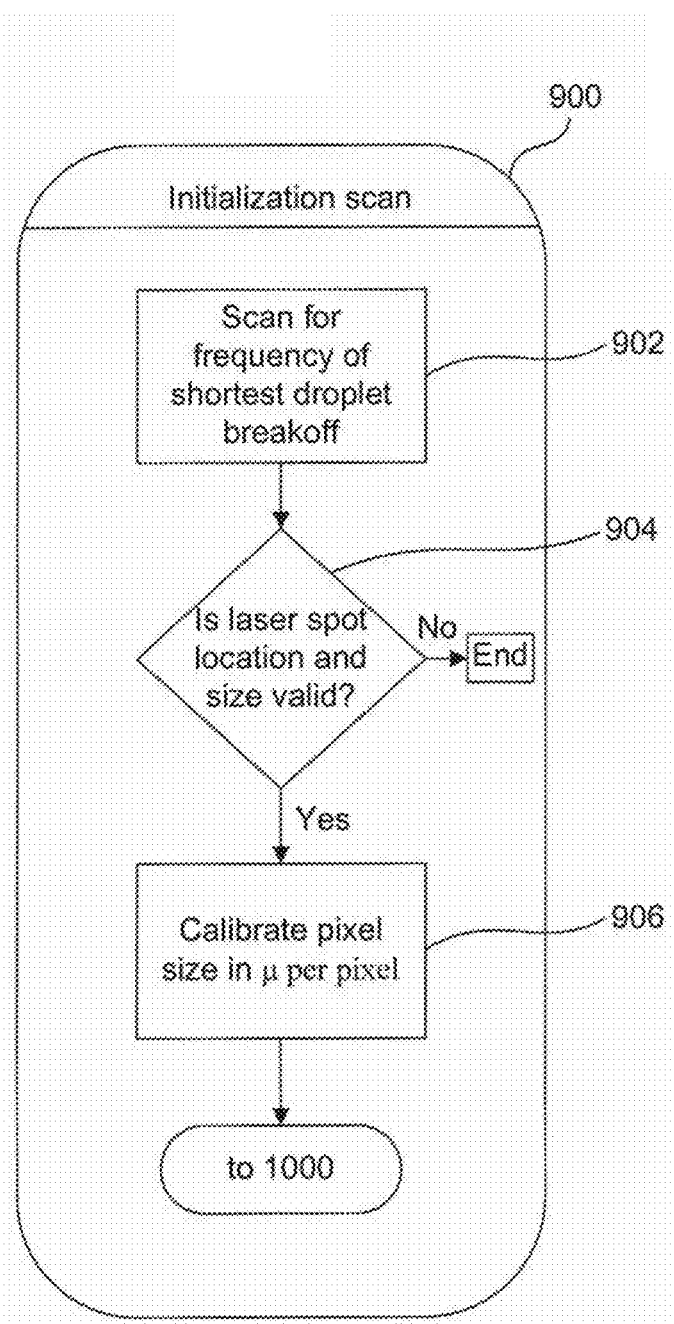
FIG. 9A is a flowchart showing a method of conducting an initialization scan.

FIG. 9A is a flowchart showing method 900 of conducting an initialization scan. Method 900 includes a step 902 for scanning the oscillator 10 through a range of frequencies to determine the shortest droplet break-off; a step 904 to confirm that the laser spot location and size are valid (or plausible); and a step 906 to calibrate the pixel size in microns per pixel.

Figure 9B:
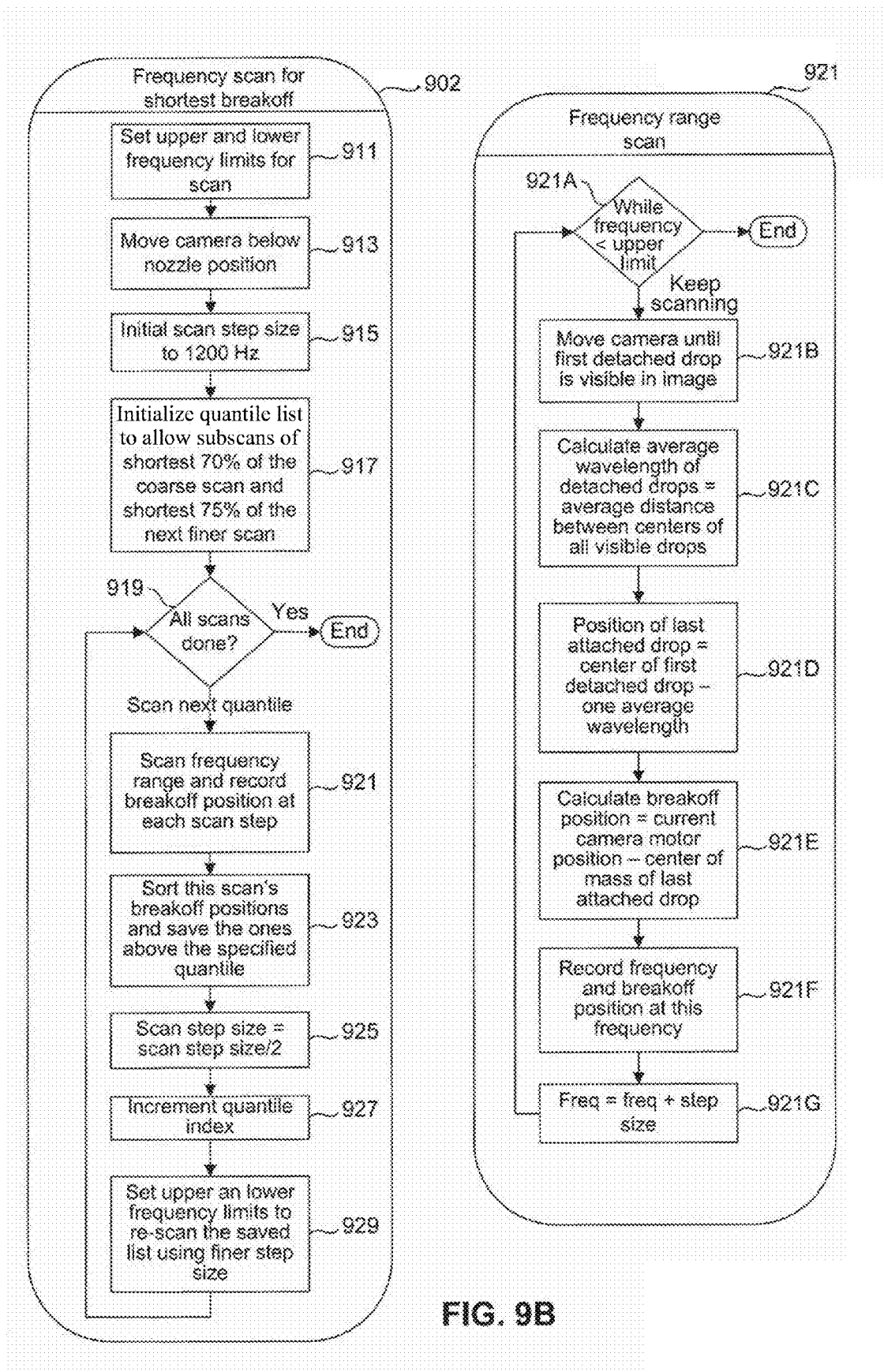
FIG. 9B is a flowchart showing a sub-protocol of the method shown in FIG. 9A.

FIG. 9B is a flowchart showing sub-protocol step 902 of method 900 shown in FIG. 9A. Sub-protocol step 902 can be programmed into a processor for determining the shortest droplet break-off of a stream exiting the flow cytometer nozzle. In general what is done in this sub-protocol is the oscillator 210 (FIG. 2) is set at given frequency and the stream 207 is scanned by the camera 202 to determine where the drops 213 break off from the stream 214. Once this location 214 is found, the oscillator frequency is changed by a given increment and the stream is scanned again by the camera. This process is repeated until the break-off point stops moving toward the nozzle and begins to move away from the nozzle. The frequency which causes the point of closest position of break-off to the nozzle is the optimal frequency. The oscillator frequency is then held at this optimal frequency and the stream is scanned again at finer resolution until the point 214 (FIG. 3) at which break-off just begins is determined.

In more detail in step 911, the program sets upper and lower oscillator drive frequency limits for the oscillator frequency scan. In step 913, the camera is moved below the nozzle position. In step 915, the scan step size is initially set to 1200 Hz. In alternative embodiment, the scan step size can be set to an alternative frequency. In step 917, a quantile list of the position of first drop separation is initialized in memory so as to record the subscans of the shortest 70% of the course scan and the shortest 75% of the next finer scan. In step 919, the program asks if all scans are done. If they are, the program ends. Otherwise, the program proceeds to step 921, where the program scans the stream with the camera over each frequency in the oscillator frequency range and records the break-off position at each frequency increment. This series of steps generates a series of measurements which forms a distribution about the point of closest approach of the break-off point to the nozzle. It is this distribution that will be divided into quantiles and the upper and lower quantiles discarded.

Step 921 is performed by the protocol outlined in steps 921A-921G. Specifically, while the frequency is less than the upper limit 921A, the scans continue. At each set oscillator frequency, the camera is moved until the first detached drop is visible, in step 921B. Then, in step 921C, the average distance (termed a drop wavelength) between detached drops is calculated by averaging the distance between centers of all visible drops. In step 921D, the position of the last attached drop is calculated by subtracting one average drop wavelength from the center of the first detached drop. In step 921E, the break-off position is calculated by subtracting the center of mass of the last attached drop from the current camera motor position. In step 921F, the oscillator frequency and break-off position are recorded. In step 921G, the oscillator frequency is incremented, and the protocol returns to step 921A.

Sub-protocol step 921 then moves to step 923, where the scan's break-off positions are sorted and the ones above the specified quantile in the distribution of break-off points are saved. In step 925, the scan step size is incremented by one half. In step 927, the quantile index into memory is incremented. In step 929, the upper and lower frequency limits are set to re-scan the saved list using a finer step size.

Figure 9C:
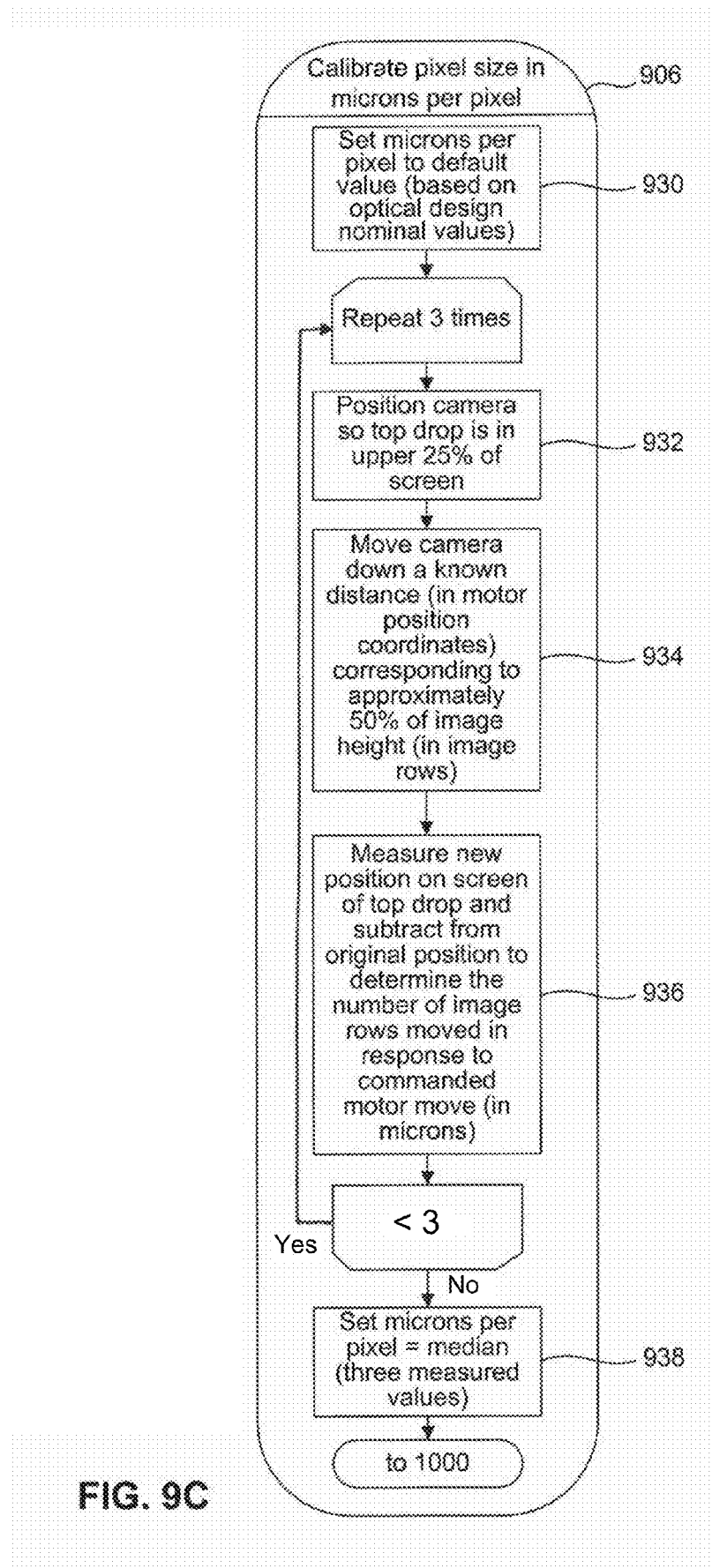
FIG. 9C is a flowchart showing a sub-protocol of the method of shown in FIG. 9A.

FIG. 9C is a flowchart showing sub-protocol step 906 of the method of shown in FIG. 9A. In sub-protocol 906, the microns per pixel of image is measured and calibrated. In step 930, the microns per pixel are set to a default value (based on optical design nominal values). Steps 932, 934, and 936 are then repeated three times. In step 932, the position of the camera is set so the top drop is in the lower 25% of the screen. In step 934, the camera is moved down a known distance (in motor position coordinates). In one embodiment, the distance moved corresponds to approximately 50% of the display screen (in image rows). In step 936, the new position on screen of top drop is measured and the original position is subtracted to determine the number of image rows moved in response to commanded motor move (in microns). After repeating steps 932, 934, and 936, microns per pixel is set to equal the median of the three measured values.

Figure 10A:
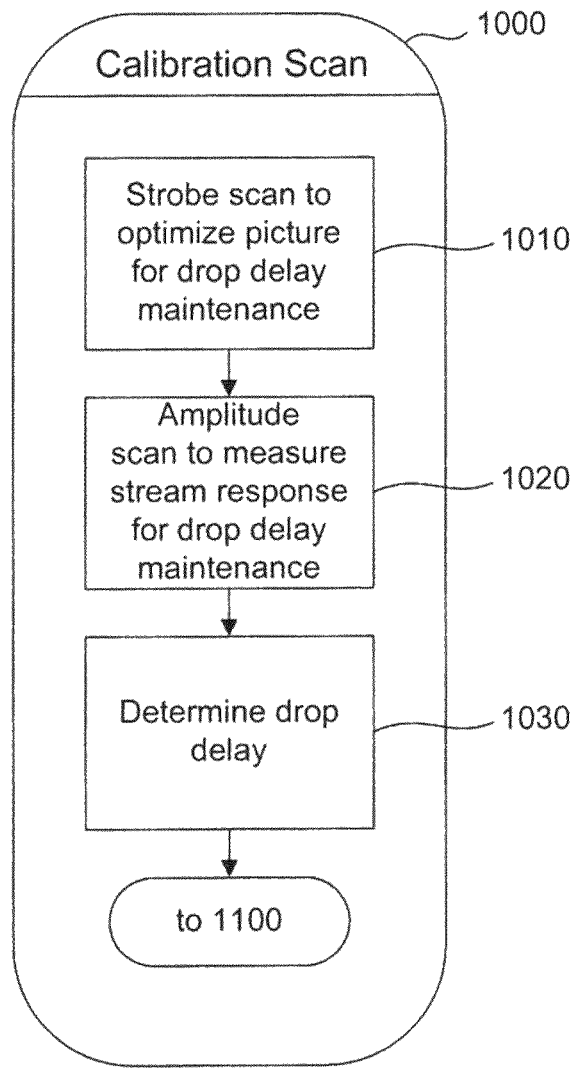
FIG. 10A is a flowchart showing a method of conducting a calibration scan.

FIG. 10A is a flowchart showing a method of conducting a calibration scan. Next, in general, the position of the break-off point is affected by not only the frequency of the oscillator but also the amplitude of the driving frequency. As a result a series of changes in oscillator amplitude are made and the effect of the changes on the repeatability of the image determined. Similarly the strobing of the image is also varied and the effect of the strobe changes on the repeatability of the image determined. These steps together are termed drop delay maintenance. Step 1010 (strobe scan to optimize picture for drop delay maintenance) and step 1020 (amplitude scan to measure stream response for drop delay maintenance) are steps related to the maintenance for the set drop delay (step 1100), are known in the art, and are therefore not discussed in any detail herein.

Figure 10B:
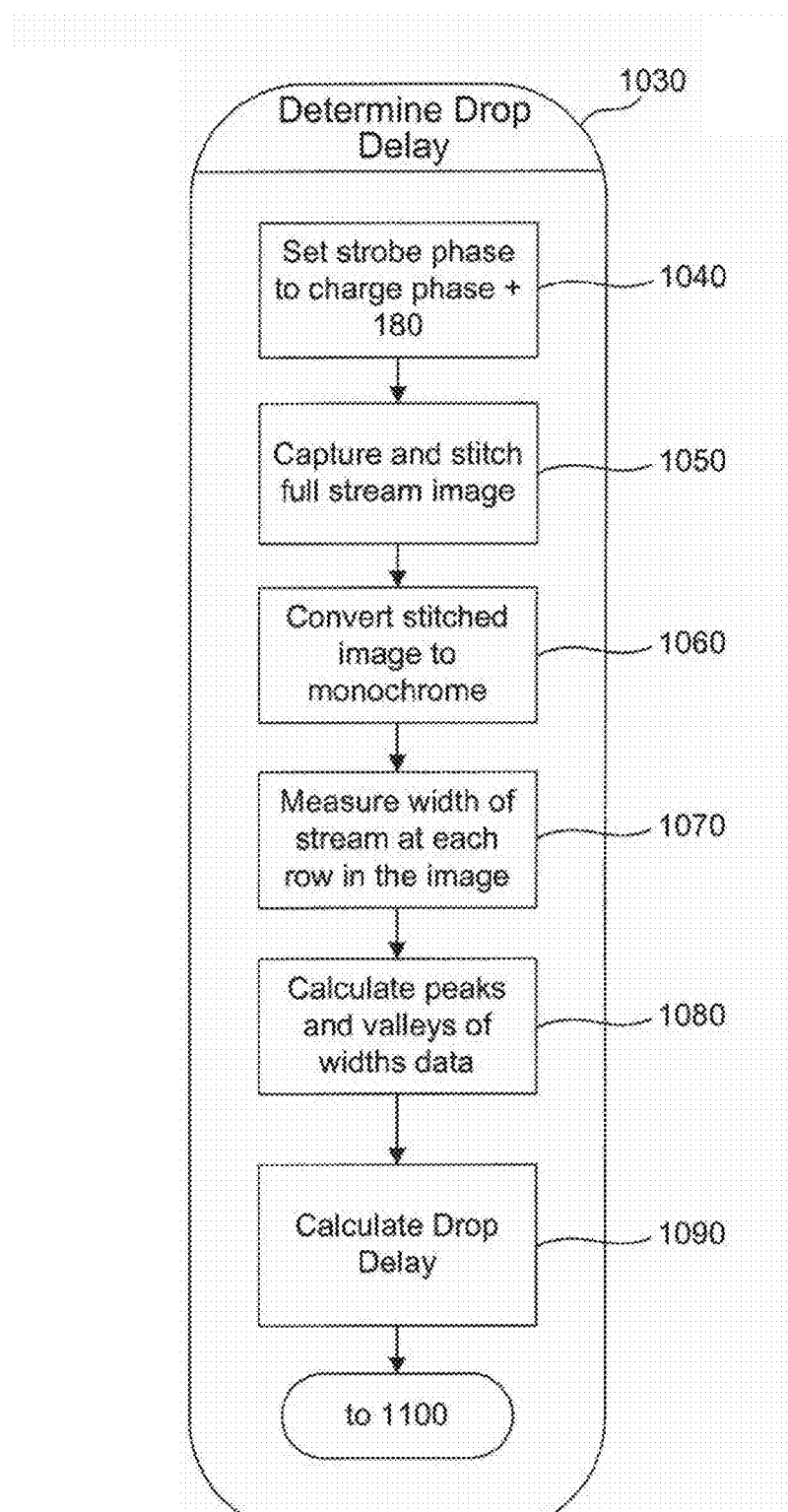
FIG. 10B outlines the steps of determining drop delay in accordance with one embodiment of the present invention.

Step 1030 provides an exemplary algorithm for determining drop delay. FIG. 10B outlines the steps of determining drop delay in accordance with one embodiment. In step 1040, the strobe phase (the position of the application of the camera strobe relative to the peaks in the drop wavelength) is set to be the charge phase (the position at which occurs the application of charge to the stream relative to the peaks in the drop wavelength) plus 180°. In practice, the charge phase is typically set to be slightly offset from the reference phase (i.e., the phase of the oscillator drive frequency). In step 1050, a movable camera is used to capture a plurality of images of the stream, and a processing unit is used to stitch the plurality of images to form a full stream image.

Figure 3:
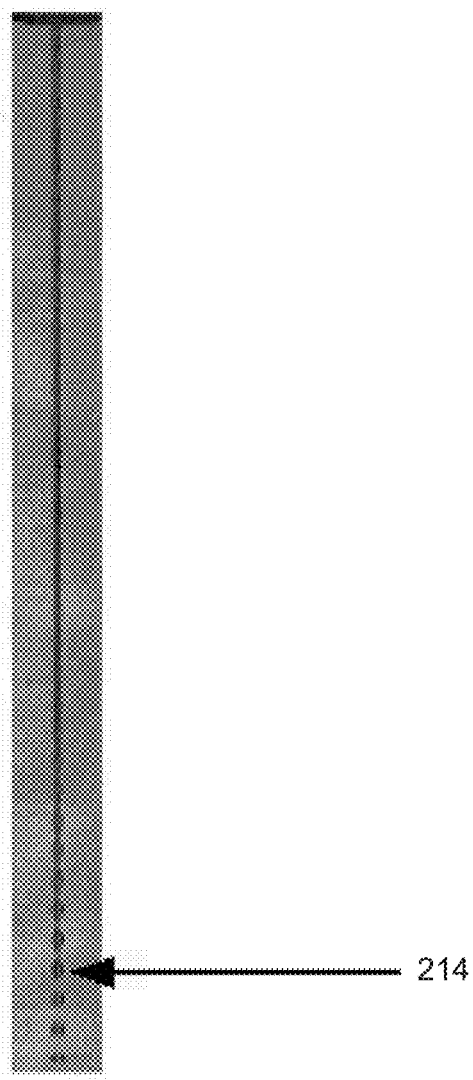
FIG. 3 is a stitched image prepared from a plurality of images taken from a camera in a flow cytometer.
Figure 10C:
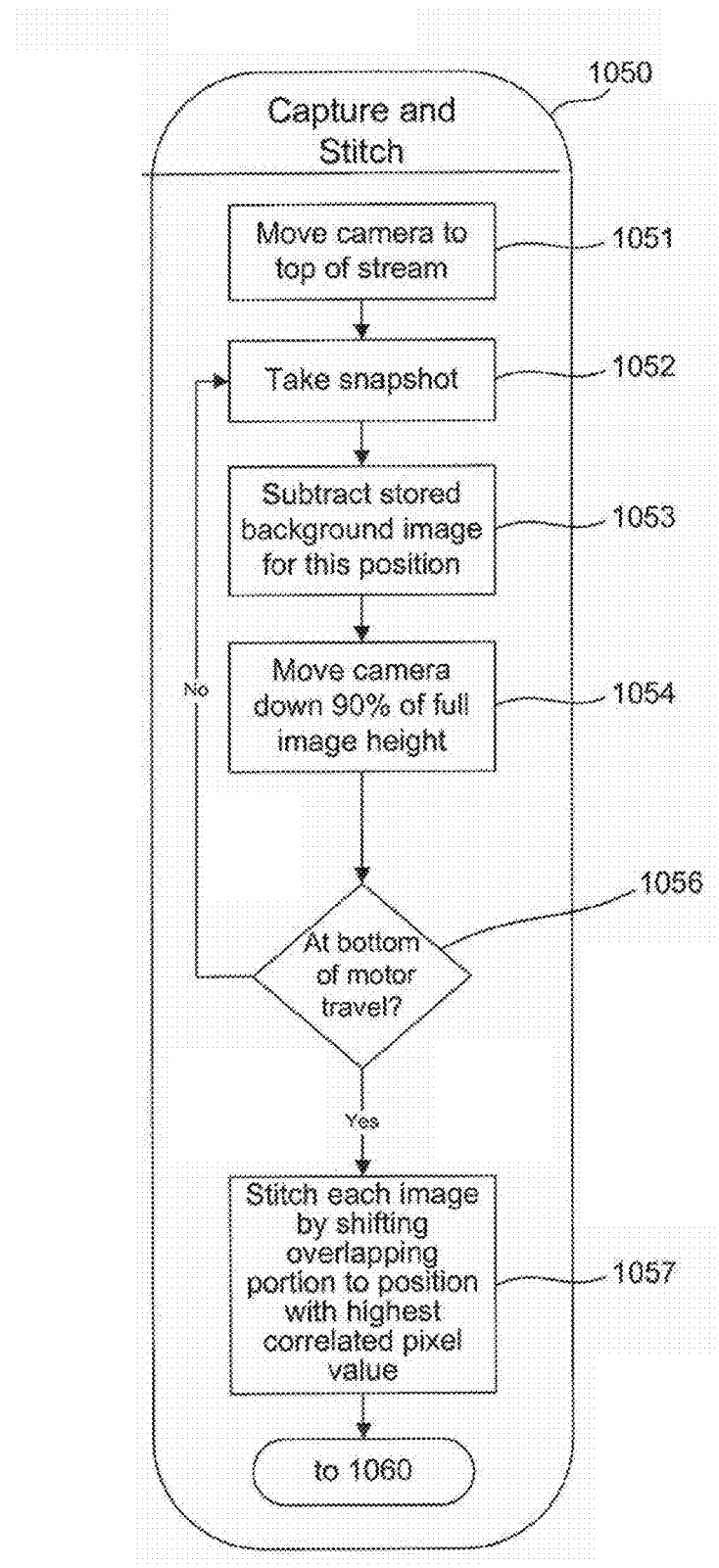
FIG. 10C is a sub-protocol to capture and stitch a full stream image in accordance with one embodiment of the present invention.

FIG. 10C is a sub-protocol of step 1050, outlining the steps to capture and stitch a full stream image in accordance with one embodiment of the present invention. FIG. 3 shows an exemplary stitched image, which was prepared from a plurality of images taken from a camera in a flow cytometer in accordance with the present invention. With reference to flow cytometer 200 of FIG. 2, camera 202 is moved to a home position (i.e., the top of stream 207), step 1051, where the first image is taken, step 1052. In step 1053, the stored background image is subtracted for the position. In step 1054, camera 202 is moved down stage 201 approximately one screen-full, but leaving a specified amount of overlap (e.g., 10% of an image). A subsequent image is then taken. This process is repeated (step 1056) until camera 202 images only droplets 213 (i.e., camera 202 has moved past break-off point 214 and is at the bottom of motor travel).

Images near the top of stream 207 can have poorly defined width signatures, which can complicate the extraction of peak information. For this reason, when operating with a low drive amplitude setting of the oscillator, the drop drive voltage setting in one embodiment is increased while taking the first several images. Increasing the drop drive voltage has the effect of increasing the amplitude of the stream perturbations, but does not shift the droplet position. As such, the drop count remains consistent. However, the drive voltage should be decreased to its operational setting before moving the camera too far down the stream because the drive voltage setting will change the absolute break-off of the droplets.

In one embodiment, there is provided a means for taking a plurality of images of a flow cytometer stream by performing the following program, written in C++ programming language:

```
Calibrate micronsperpixel
//micronsperpixel is a measurement of the number of microns of
stream //length represented by each image pixel
Move camera to home
do
   if near nozzle
   bump up drop drive amplitude
```

```
    else
        set drop drive amplitude to operational
    end if
    take (horizontally) centered picture
    if only drops in picture break
    command motor to move to curpos + (1−overlap)*1280*
    micronsperpixel
while
```

It is understood that the above computer program, and any other computer program presented herein, is merely exemplary. Other logic, in the same or other programming language, can be used to achieve the same purpose.

The method then moves on to step 1057, where the images are stitched by overlapping portions to the position with the highest correlated pixel value, as further discussed below. The plurality of images is stitched together using digital image processing algorithms. Typically, the images are poorly aligned. Vertical alignment is a function of the precision of the motor movement, the consistency of the camera stage (camera pointing) and the estimated value for microns per pixel. The horizontal alignment is a function of motor travel and stream vertical alignment, and tends to be off by several tens of pixels.

To find the best image match, each of the images gathered in the first phase is fitted to the previous image immediately above to find the best alignment in pixel space. To accomplish the fit, the bottom image is moved with respect to the upper image to find the best location (in top image pixel space) in terms of fit. The images are sampled in a correlation window that is common to both images. In one embodiment, there is provided a means for stitching a plurality of images of a flow cytometer stream by performing the following program, written in C++ programming language, wherein in the algorithm below: (dr) is ½ the width of the row search space, and (dc) is ½ the column search space for the image correlation; the values of rowoffset and rowdepth are chosen such that the image can be move downward and leftward without the correlation window of the second image leaving the first; the function ordered-pixels transforms a rectangular domain of an image (defined by [rowbegin, rowend, colbegin, colend]) into a vector by unwrapping each row scanline consecutively.

```
startrow = 1280*(1−overlap)
// Bottom image pixels
vb = orderedpixels([rowoffset, rowoffset+rowdepth, width/3, 2*width/3])
for row = startrow − dr to startrow + dr
    for col = −dc to dc
        // Top image pixels
        vt = orderedpixels([startrow + rowoffset + row,
                           startrow + rowoffset + row + rowdepth,
            width/3+col, 2*width.3+col)
        c=( vt, vb)\(| vt || vb |)
    end for
end for
return row and col with max c.
```

It is understood that the above computer program, and any other computer program presented herein, is merely exemplary. Other logic, in the same or other programming language, can be used to achieve the same purpose.

The images are often mismatched upon first processing of the images. For example, with a 400×1280 pixel image, and a 10% overlap, it is predicted that the bottom image will fit at pixel offset g=(0, 1152). For all pixels within the box that stays fixed to the second image space, the pixels of the two images are treated as two large vectors (vt and vb), with entries defined by the pixel colors (unrolled by row and column). The correlation factor is determined by computing (and normalizing) the dot product of the two vectors, c=(vt, vb)\ (|vt||vb|). This factor (0≤c≤1) determines how well the two images align for a given offset g. The fit is largest when the two images are exactly the same.

The factor g is moved within the given correlation window and the best offset is used as a stitched offset for these two images. This process continues down the stream until all images are correlated to the one above. As the process continues, the stitching offsets are kept relative to the first image so as to place the entire sequence into a single image (by simply copying pixels from relative to top image space). Where images overlap, the two sets of pixels are averaged, which allows visual inspection of the image to determine the quality of the stitching.

Due to the periodic nature of the stream image, an initial guess must be good enough so that it is within a half of a drop wavelength of the correct pixel offset. Otherwise a given waveform might potentially be matched to the wave before or after the correct one, thus either inserting or deleting a period from the system.

Figure 10D:
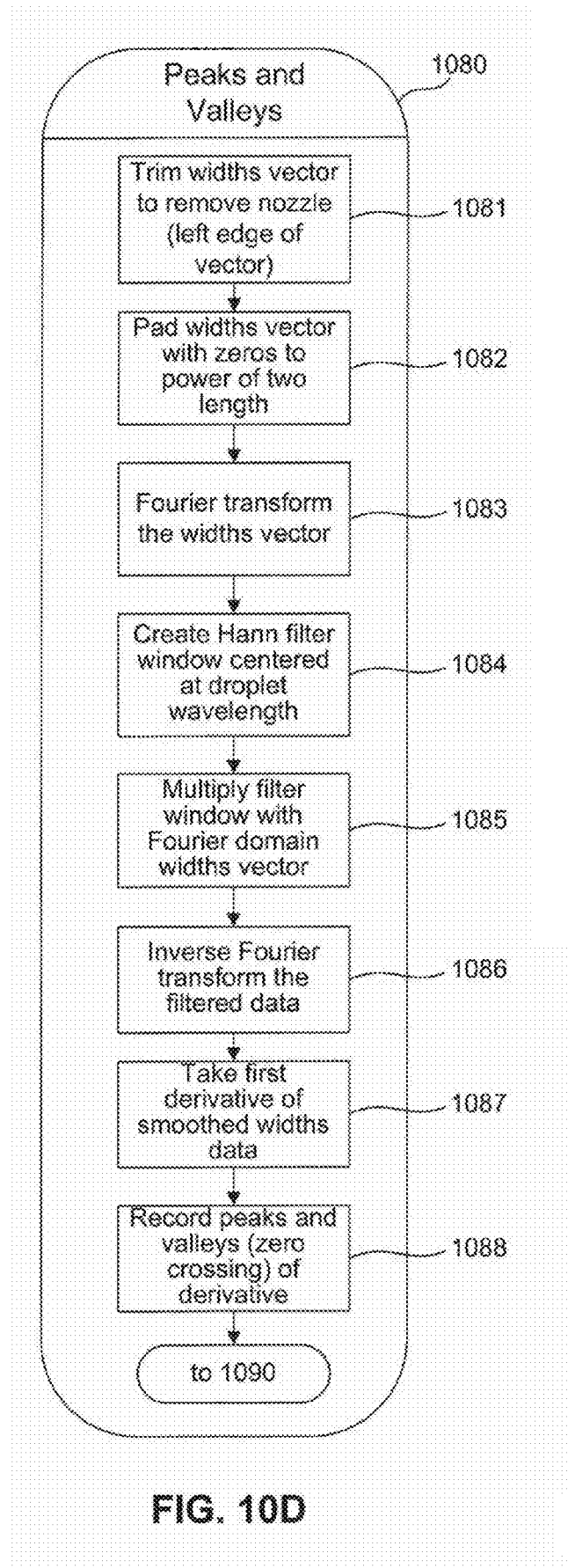
FIG. 10D is a sub-protocol to calculate peaks and valleys of a widths plot in accordance with one embodiment of the present invention.

After the image is stitched together, as shown in FIG. 3, the width of the stream at each line in the image is extracted into a widths plot (FIG. 4) that is used to detect the peaks and valleys of the stream width image. FIG. 10D is a sub-protocol to calculate peaks and valleys of a widths plot in accordance with one embodiment of the present invention.

Figure 4:
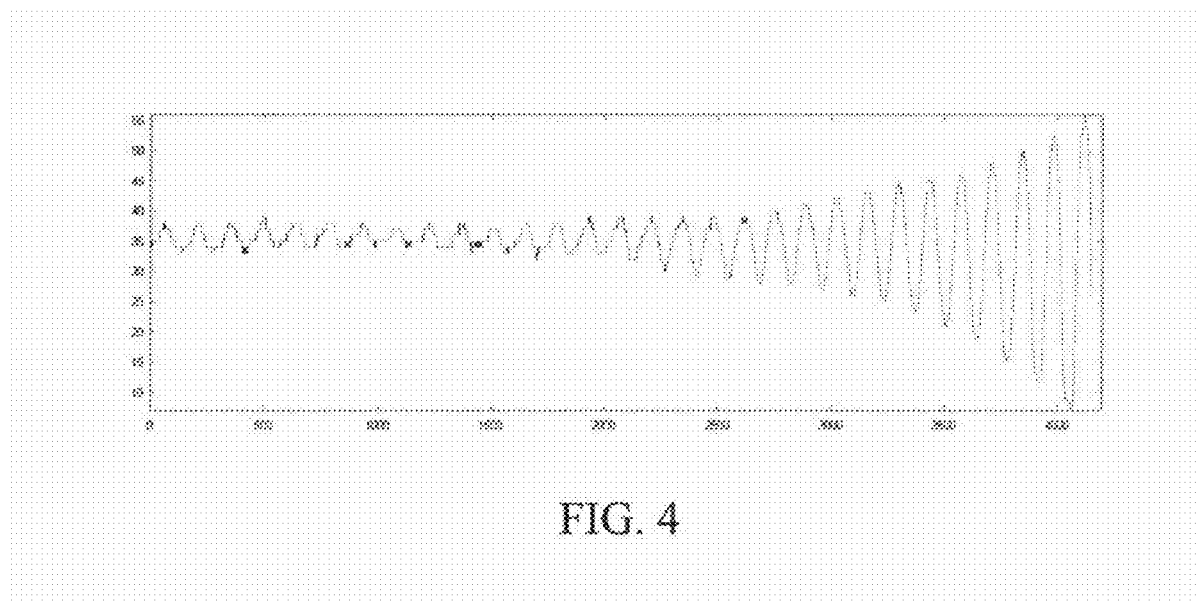
FIG. 4 is an example widths plot measured from a stitched image, such as the image shown in FIG. 3.

FIG. 4 is an example widths plot measured from a stitched image, such as the image shown in FIG. 3. Assuming that the speed of the particles is closely tied to the wavespeed, the count of these peaks allows for an estimate of the amount of time a particle takes to traverse from interrogation (or laser intercept 250) to break-off point 214, and thus allows for the calculation of drop delay.

In one embodiment, the stitched image is converted to black and white via standard processing (histogram equalization, Gaussian smoothing, and row-by-row mean value thresholding). The resulting black and white image, where white represents the background population and black the stream population, is then converted into a stream widths plot. In one embodiment, there is provided a means for converting a stitched image into a black and white image by performing the following program, which is written in C++ programming language:

```
For each row
    Width(row) = 0
    // scan from left edge until we hit stream pixels
    While pixel(row,col) is WHITE and column < width
        Next column
    End while white pixels
    // now count all contiguous black pixels as part of stream width
    While pixel(row,col) is BLACK and column < width
        Increment width(row)
    End while black pixels
End for
```

It is understood that the above computer program, and any other computer program presented herein, is merely exemplary. Other logic, in the same or other programming language, can be used to achieve the same purpose.

Since the widths plot is taken from the monochrome image, it is fairly noisy. In particular, near the nozzle where the amplitude of the oscillator on the stream is low, the signal-to-noise ratio of the widths plot is not very good. From row to row, the threshold algorithm results in a few pixels being assigned to the wrong category (either false positive or false negative) resulting in a very noisy signal. Trying to find peaks and valleys on this signal would be very difficult. As such, in one embodiment, a Fourier analysis is conducted to filter the widths plot in order to extract the relevant signal characteristics (peaks and valleys of the main signal). Specifically, a Fourier analysis for frequency domain filtering is conducted to filter (or smooth) the widths plot. Filtering in the Fourier domain allows for the retention of selected frequencies and rejection of others via Fourier transform of the spatial domain signal, application of a simple windowing function to the frequency domain signal, followed by an inverse Fourier transform back to the spatial domain. Such Fourier analysis is outlined in FIG. 10D.

Preprocessing can be useful to effectively filter a discrete signal using a windowing function. In step 1081, the widths plot is trimmed to remove the nozzle area of the widths plot (i.e., the left edge of the widths plot). Efficient implementations of the Fast Discrete Fourier Transform operate on data whose length is an even power of two. In step 1082, the original data is padded from its original length with zeros to the next higher power of two length. Sudden transition from the signal values to a padding value would introduce step function to the data if care is not taken, and would result in Gibbs ringing of the transformed data. In order to pad the data with as smooth of a transition as possible, the data is extended from the left edge since the measured data at row zero converges (to the left) to a DC offset equal to the mean width of the stream. In one embodiment, there is provided a means for padding the widths plot by performing the following program, which is written in C++ programming language:

```
Calculate stream mean width
Calculate NN = next power of two length, from widths.size( )
Pad = NN – widths.size( )
For i=0 to pad
    paddedWidths[i] = mean width
end for
for i=pad to NN
    paddedWidths[i] = widths[i–pad]
end for
```

It is understood that the above computer program, and any other computer program presented herein, is merely exemplary. Other logic, in the same or other programming language, can be used to achieve the same purpose.

In step 1083, a discrete Fourier transform is performed on the widths plot. While the flowchart of FIG. 10D illustrates the use of a Fourier transform and Hann filter analysis, alternative filtering techniques can be designed to achieve the same objectives. Windowing is then performed to filter the data. The simplest filter window is the rectangular window—zero for stopped frequencies, one for passed frequencies. This window produces ringing in the inverse transformed signal, though, and can make it difficult to resolve either a) signals whose relative strength is very different, or b) signals whose frequencies are too close together. Instead of a rectangular window, an alternative embodiment uses a commonly used moderate windowing function called a Hann window. In step 1084 a Hann filter window is created and centered at the droplet wavelength. The Hann window (function provided below) reduces spectral leakage compared to the rectangular window, but still has good sensitivity for low-bandwidth signals like the widths plot:

$$w(n) = 0.5\left(1 - \cos\left(\frac{2\pi n}{N-1}\right)\right)$$

The center frequency of the Hann window is chosen to match the frequency of the first peak on the Fourier transformed data. The width of the Hann window can be chosen fairly arbitrarily to encompass most of the first peak information for a given nozzle size (e.g., 70 micron nozzles), while excluding the secondary and higher order peaks in the frequency data. The left edge and right edge cutoff values of the filter are symmetric around the peak and cutoff frequencies whose magnitudes are less than about 10% of the magnitude of the peak. The width of the filter window can be parameterized to deal with other nozzle and stream information.

Figure 5A:
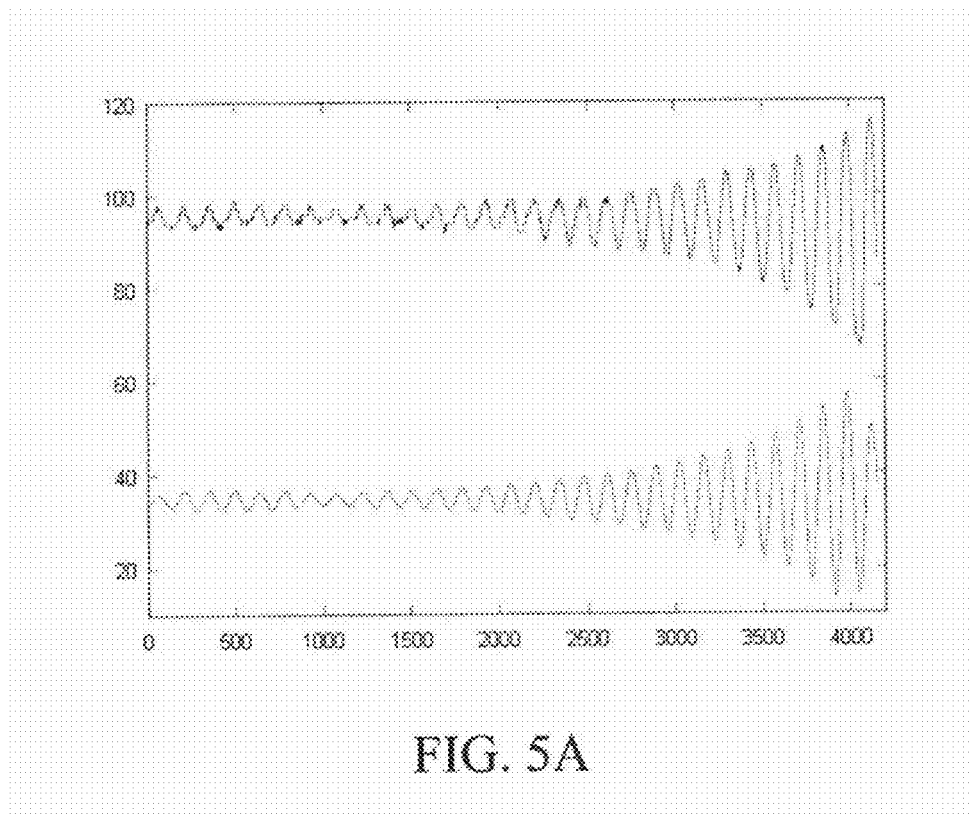
FIG. 5A shows the original widths plot of FIG. 4 and a filtered (smoothed) widths plot. The original widths plot has been offset by 60 to allow both plots to be shown without overlap.
Figure 5B:
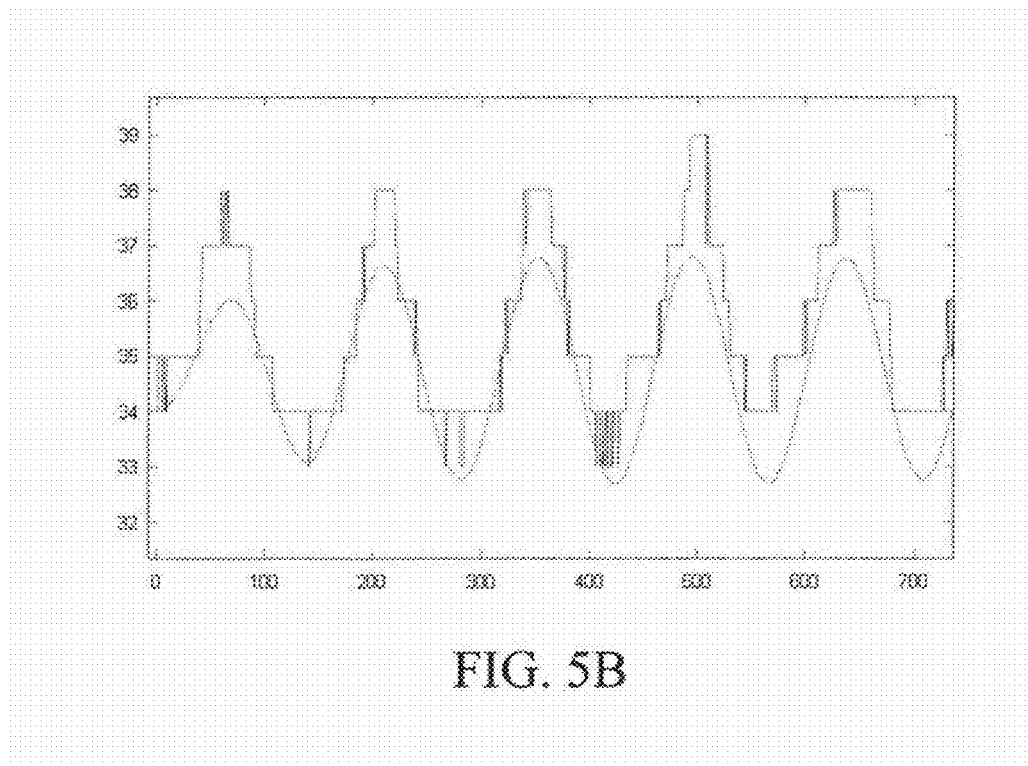
FIG. 5B is a close-up of the plot of FIG. 5A, showing data near the nozzle, overlaid to show both raw and filtered (smoothed) data.

In step 1085, the data is filtered by multiplying the filter window by the frequency domain padded data. Then, in step 1086, the frequency domain data is transformed back to the spatial domain with an inverse-transform function. FIG. 5A shows the original widths plot of FIG. 4 and a filtered (smoothed) widths plot. The original widths plot has been offset vertically to allow both plots to be shown without overlap. FIG. 5B is a close-up of the plot of FIG. 5A showing data near the nozzle, overlaid to show both raw and filtered (smoothed) data. Overall, the filtered data has peaks and valleys that track very closely to the original data, but which have smooth inflections allowing the location of the peak values to be calculated.

After filtering the peak data, the derivative of the filtered data (by simple difference) is computed, in step 1087, and the zero crossings are identified, in step 1088. The peaks are identified by selecting the zero-crossings that are decreasing left to right. At the nozzle, an extrapolation is performed because the last waveform or two can be ill formed due to the presence of the nozzle. In one embodiment, there is provided a means for finding peaks by performing the following program, which is written in C++ programming language:

```
//let sw be the smoothed width vector.
resize(ds, length(sw)–1)
for i = 1 to length(ds)
    ds = sw(i) – sw(i–1)
end for
for i = 2 to length(ds)
    if (ds(i–1) >= 0 and ds(i) < 0) push_back(peaks, ds(i))
end for
```

It is understood that the above computer program, and any other computer program presented herein, is merely exemplary. Other logic, in the same or other programming language, can be used to achieve the same purpose.

Figure 10E:
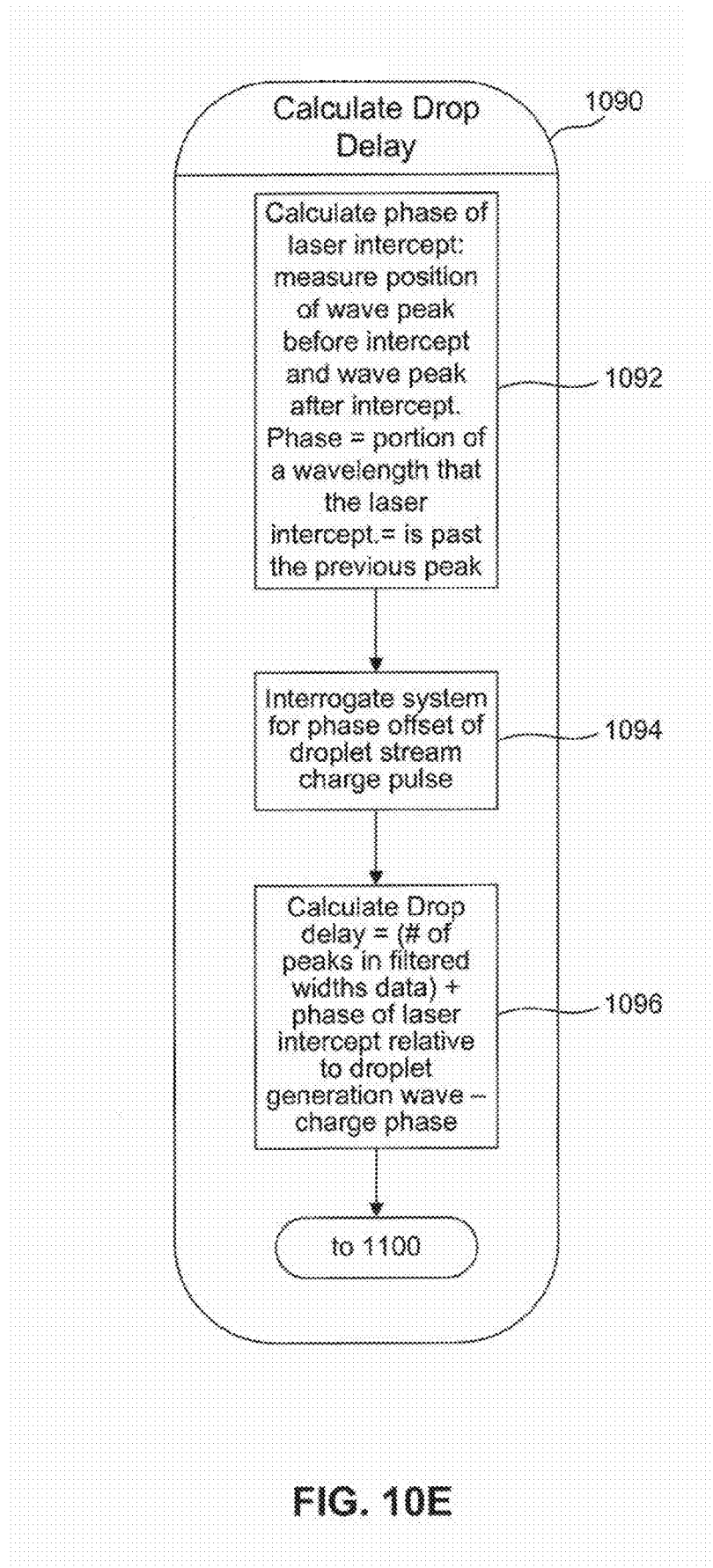
FIG. 10E is a sub-protocol to calculate drop delay in accordance with one embodiment of the present invention.

FIG. 10E is a sub-protocol to calculate drop delay in accordance with one embodiment of the present invention. The method of calculating drop delay is outlined as follows. In step 1092, the phase of the laser intercept relative to the oscillator frequency is calculated by measuring the position of the widths plot peak before the intercept and the widths plot peak after the intercept. The phase is then set to equal the portion of the wavelength between the peaks that the laser intercept as measured from the previous peak. In step 1094, the system is interrogated to identify the phase offset of the droplet stream charge pulse. The charge phase is typically offset from the reference drive frequency to account for the ramp-up time of the charge pulse. In step 1096, the drop delay is calculated by setting the drop delay to equal the number of peaks in the filtered widths data, plus the phase of the laser intercept relative to the droplet generation wave, minus the charge phase, plus a bias component. The protocols of steps 1092, 1094, and 1096 will be further understood based on the description provided below.

In one embodiment, a method for calculating drop delay accounts for phase variables such as the phase of the oscillator, charge electrode, strobe system, camera images, and/or laser. Specifically, to obtain the fractional part of drop delay, various phase variables within the system are reconciled. These variables can be ignored when using beads to experimentally determine drop delay, as in prior art systems, but should be accounted for in the predictive methods of the present invention.

Figure 6:
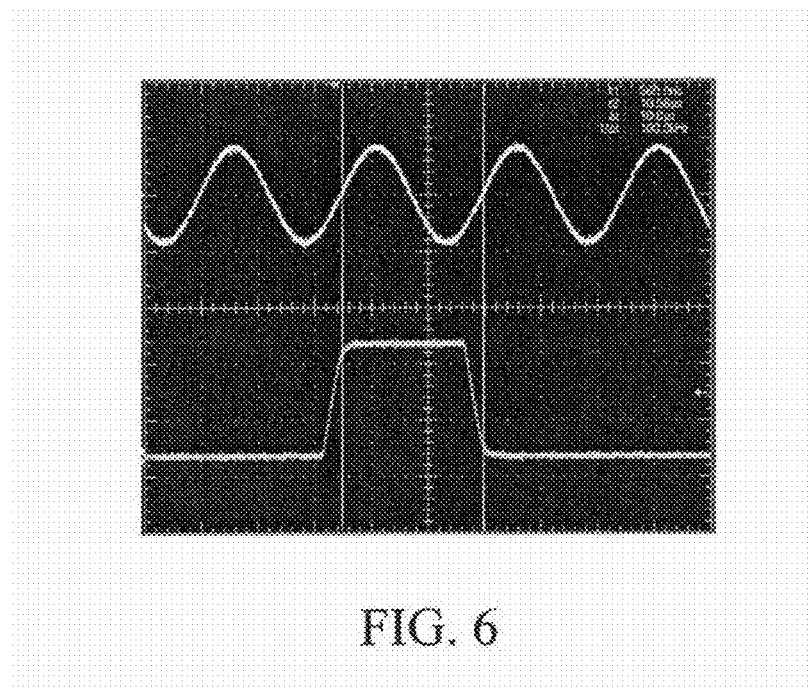
FIG. 6 shows how a charge window (bottom) is at a specified phase of the oscillator cycle (top).

The appropriate charge phase is selected by moving the charge phase window until clean sort streams are obtained. This process effectively aligns the offset between the drop drive clock and charge to optimize droplet charge. A key realization is that the droplet charge pulse can occur only at a discreet set of times, namely once per drop drive period. FIG. 6 shows how a charge window (bottom) is at a specified phase of the oscillator cycle (top).

In practice, the basic life cycle for an event is: 1) a timestamp is assigned at the laser intercept; 2) drop delay is added; and 3) the selected droplet is charged. Specifically, at the moment of laser interrogation, a high precision time-stamp is added to the event. The timestamp is passed into software, which estimates the eventual drop that the particle will end up in. The formula for this is: drop=(intercept time+drop delay) div (drop drive period), where div is integer division (throw away remainder). By choosing drop delay, a mapping is created between a moving window in time (exactly one period long) and a drop number. Each subsequent window in time will map to the subsequent drops.

The effect of changing the fractional part of drop delay is to slide the window in time of events that are predicted to land in a drop. When the calculation of the fractional part is wrong, the system effectively predicts the "pre drop" incorrectly, and events that fall within these times map to more than one droplet, or to a droplet other than the desired.

With respect to the laser phase, a very simple starting point for illustrating the effect of laser phase is to consider the case when the laser intercepts at the valley between two peaks, for a picture taken at zero strobe phase relative to drop drive period. A basic assumption (not always strictly true) is that such a region centered around a droplet peak eventually contracts (as it moves downstream) to form a droplet (i.e., the "pre-drop").

Consider a hypothetical particle passing the laser at an instant. Its timestamp would mark the beginning of a time interval that is desired to map into a particular drop. Particles at the top of the "pre-drop" would pass the laser at one period later, so it is desired to arrange the drop delay such that the entire interval in time maps (under the div operation) to the same drop. This arrangement is the essence of the fractional part of drop delay. The timestamp on such a particle would have a timestamp that is a perfect integer multiple of the drop drive period. Under the div operation, all times that follow within the period would lose their remainder and map to the same drop as this first particle.

The primary introduction of fractional drop delay is to account for the case when the laser is not exactly at the beginning of a "pre drop" at phase zero. For example, if the laser were instead, at the center of the bulge in the stream. All particles would hit this laser at ½ of a period earlier than they would if the laser were centered on a trough between bulges of the stream. To account for this translation in laser position, in one embodiment, the shift is accounted for by artificially adding ½ A of a period to the ADC time:

$$\text{drop}=(\{\text{intercept time}+\tfrac{1}{2}\text{ period}\}+\text{drop delay})\text{div (drop drive period)}$$

Practically, however, it is not possible to change the ADC time stamp given to an event. Instead, the associativity of addition is used to absorb this fractional offset into the drop delay:

$$\text{drop}=(\text{intercept time}+\{\tfrac{1}{2}\text{ period}+\text{drop delay}\})\text{div (drop drive period)}$$

As such, the delay has a fractional component. If the laser is at some other fractional offset (besides ½), the same procedure is followed. Of course, within a given period it is very unlikely that more than one particle will pass the laser. However, the procedure above still applies since the count of the last attached droplet is incremented by one each period.

With respect to the charge phase, since a droplet will break off cleanly at some (unknown) phase during the period, it is possible (depending on charge phase) that the actual drop that is charged for sorting can be the one that is still connected in the image at phase zero, or the next higher (for later charge phases). To enable the image processing to clearly detect which is the case, the image is taken at exactly the charge phase. In this way it can be detected which drop is to be selected for charging. Taking the image at a later phase effectively moves the laser up the "pre drop" by the corresponding fractional phase. To make up for this effective move, the algorithm effectively moves the laser back down by subtracting the fractional movement, and the final drop delay estimate is:

$$\text{drop delay}=\{\text{fractional laser offset}+\text{integral drop delay}-\text{fractional charge phase}\},$$

where the image is strobed at exactly the charge phase

A final accommodation can be made for an experimentally observed bias. For alternative nozzle sizes, a bias can exist. Such bias can be experimentally determined and can be deduced to an algebraic function in order to account for the bias (bias=aX+b). For example, the bias for a 70 micron nozzle, for example, is set as a function of:

$$-0.015465X+0.891189, \text{ where } X=0.1(\text{break-offMicrons}-\text{charge}/360*\text{lastWaveLenMicrons})/\text{avg\_velocity}.$$

This variable is basically the time from nozzle to break-off in 10 s of microns (roughly a period at 100 k Hz).

The breadth and scope of the present invention should not be limited by any of the above-described exemplary embodiments, but should be defined only in accordance with the following claims and their equivalents.

The invention claimed is:

1. A method of calculating a drop delay in a stream of a flow cytometer, comprising:
   (a) identifying a laser position relative to a frame of reference;
   (b) determining a break-off point; and
   (c) calculating the drop delay by
      1) setting a strobe phase,
      2) imaging the stream,
      3) determining a widths plot by measuring the widths of the stream based on the image of the stream,
      4) determining the peaks in the widths plot;
      5) calculating a phase of laser intercept relative to a droplet generation wave, and 6) calculating the drop delay in response to the peaks in the widths plot, the phase of laser intercept and a charge phase.

2. The method of claim 1 further comprising the step of smoothing the widths plot.

3. The method of claim 1 wherein the step of determining of the peaks in the widths plot comprises the steps of calculating a derivative of the widths plot and recording a plurality of zero-crossings of the derivative, wherein each zero-crossing is indicative of a peak in the smoothed widths plot.

4. The method of claim 1 wherein the break-off point is the shortest break-off point.

5. The method of claim 1 wherein the step of imaging the stream comprises the steps of running a camera along a length of the stream, while taking a plurality of images of the stream; and stitching the plurality of images together to form a single image.

6. The method of claim 1 wherein the strobe phase is set to the charge phase plus 180°.

7. The method of claim 1 wherein the drop delay is also calculated in response to a bias correction factor.

8. The method of claim 7, wherein the bias correction factor is equal to a linear function aX+b, where X is the time from nozzle to break-off and parameters "a" and "b" are determined from experimental measurement of system response.

9. The method of claim 2, wherein the smoothing of the widths plot is conducted using a discrete Fourier analysis.

10. The method of claim 5 wherein a drive voltage is increased from an operational value when the camera is at about the top of the stream, and the drive voltage is decreased to an operational value as the camera is driven down towards the break-off point.

11. The method of claim 1, wherein the calculation of drop delay is used to determine when an analyte of interest has reached the break-off point of the stream.

12. A flow cytometer system for automatically calculating a drop delay, comprising:
   a camera adapted to take an image of a stream; and
   a processor adapted to
      determine a widths plot based on the image of the stream,
      determine the peaks in the widths plot,
      calculate a phase of laser intercept relative to a droplet generation wave, and
      calculate the drop delay in response to the peaks in the widths plot and the phase of laser intercept.

13. A flow cytometer system for automatically calculating a drop delay, comprising:
   a camera mounted on a precision calibrated, movable camera stage, which is adapted to take a plurality of images of a stream; and
   a processor adapted to
      stitch the plurality of images of the stream to form one entire image of the stream,
      determine a widths plot based on the one entire image of the stream,
      smooth the widths plot,
      calculate a derivative on the smoothed widths plot,
      determine zero-crossing on the smoothed widths plot,
      calculate a phase of laser intercept; and
      calculate the drop delay based on the determined zero-crossings and the calculated phase of laser intercept.

14. The flow cytometer system of claim 12 wherein the processor is further adapted to include a charge phase in the calculation of the drop delay.

15. The flow cytometer system of claim 12 wherein the processor is adapted to calculate the phase of laser intercept based on a position of a peak before a laser position and the position of a peak after the laser position in the widths plot.

16. The flow cytometer system of claim 15 wherein the processor is adapted to determine the number of peaks between the laser position and a break-off point in the widths plot.

17. The flow cytometer system of claim 16 wherein the processor is adapted to calculate the drop delay by adding the determined number of peaks between the laser position and the break-off point to the phase of laser intercept and subtracting a charge phase.

18. The flow cytometer system of claim 16 wherein the processor is adapted to calculate the break-off point from the image of the stream.

19. The flow cytometer system of claim 18 wherein the processor is adapted to calculate the break-off point by subtracting the length of the droplet generation wave from the position of the first detached droplet in the image.

* * * * *